United States Patent
Subramanian et al.

(10) Patent No.: US 8,958,524 B2
(45) Date of Patent: Feb. 17, 2015

(54) CORRECTION OF PROJECTION DATA IN RADIATION SYSTEM

(71) Applicant: Analogic Corporation, Peabody, MA (US)

(72) Inventors: Chitra Subramanian, Peabody, MA (US); Ram Naidu, Newton, MA (US)

(73) Assignee: Analogic Corporation, Peabody, MA (US)

( * ) Notice: Subject to any disclaimer, the term of this patent is extended or adjusted under 35 U.S.C. 154(b) by 182 days.

(21) Appl. No.: 13/756,288

(22) Filed: Jan. 31, 2013

(65) Prior Publication Data

US 2014/0211910 A1 Jul. 31, 2014

(51) Int. Cl.
| | |
|---|---|
| *G01N 23/083* | (2006.01) |
| *G01D 18/00* | (2006.01) |
| *G06K 9/60* | (2006.01) |
| *G01T 7/00* | (2006.01) |
| *G01N 23/04* | (2006.01) |
| *A61B 6/02* | (2006.01) |

(52) U.S. Cl.
CPC .............. *G01T 7/005* (2013.01); *G01N 23/046* (2013.01); *A61B 6/02* (2013.01); *G01N 2223/303* (2013.01)
USPC ................ 378/4; 378/207; 382/131; 382/275

(58) Field of Classification Search
USPC ........ 378/4–20, 62, 91, 98.12, 162, 204, 207, 378/210, 901; 382/128, 131, 254, 275
See application file for complete search history.

(56) References Cited

U.S. PATENT DOCUMENTS

| 7,224,763 B2 | 5/2007 | Naidu et al. | |
| 2012/0087481 A1* | 4/2012 | Litvin et al. | ................... 378/207 |

* cited by examiner

*Primary Examiner* — Anastasia Midkiff
(74) *Attorney, Agent, or Firm* — Cooper Legal Group LLC

(57) ABSTRACT

Among other things, one or more techniques and/or systems for correcting projection data representative of an object under examination to account for drift in a radiation system are provided. System drift is measured by performing a drift calibration on the radiation system. During the drift calibration, a temperature of the radiation system is measured and one or more calibration tables, such as an air table and/or offset table, are corrected based upon the measured temperature to derive a theoretical projection (e.g., indicative of measurements that are expected to be acquired from the radiation system during the drift calibration). The theoretical projection is compared to an actual projection acquired during the drift calibration to measure a degree of drift. Based upon the measured degree of drift, one or more correction factors are determined to correct and/or otherwise adjust for system drift in a projection respective of the object.

20 Claims, 5 Drawing Sheets

CORRECTION OF PROJECTION DATA IN RADIATION SYSTEM

BACKGROUND

The present application relates to the field of radiation imaging. It finds particular application with computed-tomography (CT) scanners configured to examine an object using radiation and generate a three-dimensional image of the object from detected radiation. It also relates to other radiation systems where correcting projection data to account for changes to one or more operating parameters (e.g., source voltage, source current, temperature, etc.) may be useful.

Radiation systems (e.g., also referred to as imaging systems and/or radiation imaging systems) such as computed tomography (CT) systems, diffraction CT, single-photon emission computed tomography (SPECT) systems, projection systems, and/or line systems, for example, are used to provide information, or images, of interior aspects of an object. Generally, the object is exposed to radiation comprising photons (e.g., such as x-ray photons, gamma ray photons, etc.), and an image(s) is formed based upon the radiation absorbed and/or attenuated by interior aspects of the object, or rather an amount of photons that is able to pass through the object. Generally, highly dense aspects of the object absorb and/or attenuate more radiation than less dense aspects, and thus an aspect having a higher density, such as a bone or metal, for example, may be apparent when surrounded by less dense aspects, such as muscle or clothing.

Radiation systems can be generally be divided into two classes, single energy and multi-energy (e.g., dual-energy). Single energy systems are configured to utilize a single energy spectrum to generate an image of an object and typically provide density information associated with the object or aspects thereof. Multi-energy systems are configured to utilize two or more distinct energy spectra to generate an image of an object and typically provide additional information about the object (e.g., such as density information and z-effective information).

Measurements acquired from a radiation system can vary due to changes in operating parameters (e.g., source voltage, source current, system temperature, etc.) or operating state of the radiation system, which can affect the images produced from the examination, particularly z-effective images generated by multi-energy systems. For example, a first examination of an object may yield measurements that are different than the measurements yielded from a second examination of the same object, performed several hours later, due to temperature changes of the radiation system. This may be true even when input parameters to the radiation system (e.g., specifying a desired radiation energy output, desired dosage, etc.) are held constant. The difference between the actual operating state and a reference operating state (e.g., upon which image reconstruction constraints and/or other system constraints are based) for a given set of input parameters is referred to herein as drift, system drift, and/or the like.

System drift can interfere with the ability of a user or automated process to accurately detect an area of interest (e.g., threat item, cancer cells, etc.) within the object because the area of interest may appear different (e.g., appear to have a different density, atomic number, shape, etc.) in respective images. Accordingly, systems and techniques have been devised for correcting for drift. One such technique is disclosed in U.S. Pat. No. 7,224,763, assigned to Analogic Corporation, which is incorporated herein by reference. The technique provides for using a filter, such as a copper filter, to measure drift. Based upon this measurement, correction factors are generated and applied to image data (e.g., post image reconstruction) to correct the image(s) of the object. While such a technique has proven useful, the accuracy of the technique is dependent upon the placement of the filter, which is subject to human error. Additionally, degradations in the detector array over time may reduce the accuracy of the technique.

SUMMARY

Aspects of the present application address the above matters, and others. According to one aspect, a method for correcting an object projection acquired via a radiation system is provided. The method comprises comparing a calibration projection indicative of an air scan with a theoretical projection to measure a degree of drift. The method also comprises applying a correction to the object projection representative of an object examined via the radiation system based upon the measured degree of drift to derive a corrected object projection.

According to another aspect, a method for correcting an object projection acquired via a radiation system is provided. The method comprises measuring a temperature of the radiation system during a drift calibration and computing a theoretical projection based upon the measured temperature. The method also comprises comparing a calibration projection acquired during the drift calibration with the theoretical projection to measure a degree of drift, the degree of drift indicative a change in an operating state of the radiation system relative to a reference operating state. The method further comprises applying a correction to a first object projection representative of an object examined via the radiation system based upon the measured degree of drift to derive a corrected object projection.

According to yet another aspect, a multi-energy radiation system is provided. The system comprises a radiation source configured to emit radiation and a detector array configured to detect at least some of the emitted radiation to generate at least a high energy object projection representative of an object examined via the radiation system and a low energy object projection representative of the object. The system also comprises a calibration component configured to compare a calibration projection acquired from a drift calibration with a theoretical projection to measure a degree of drift, the theoretical projection derived based upon a temperature of the radiation system during the drift calibration. The system further comprises a correction component configured to correct at least one of the high energy object projection or the low energy object projection based upon the measured degree of drift.

Those of ordinary skill in the art may appreciate still other aspects of the present application upon reading and understanding the appended description.

FIGURES

The application is illustrated by way of example and not limitation in the figures of the accompanying drawings, in which like references generally indicate like elements and in which.

DETAILED DESCRIPTION

Figure 1:
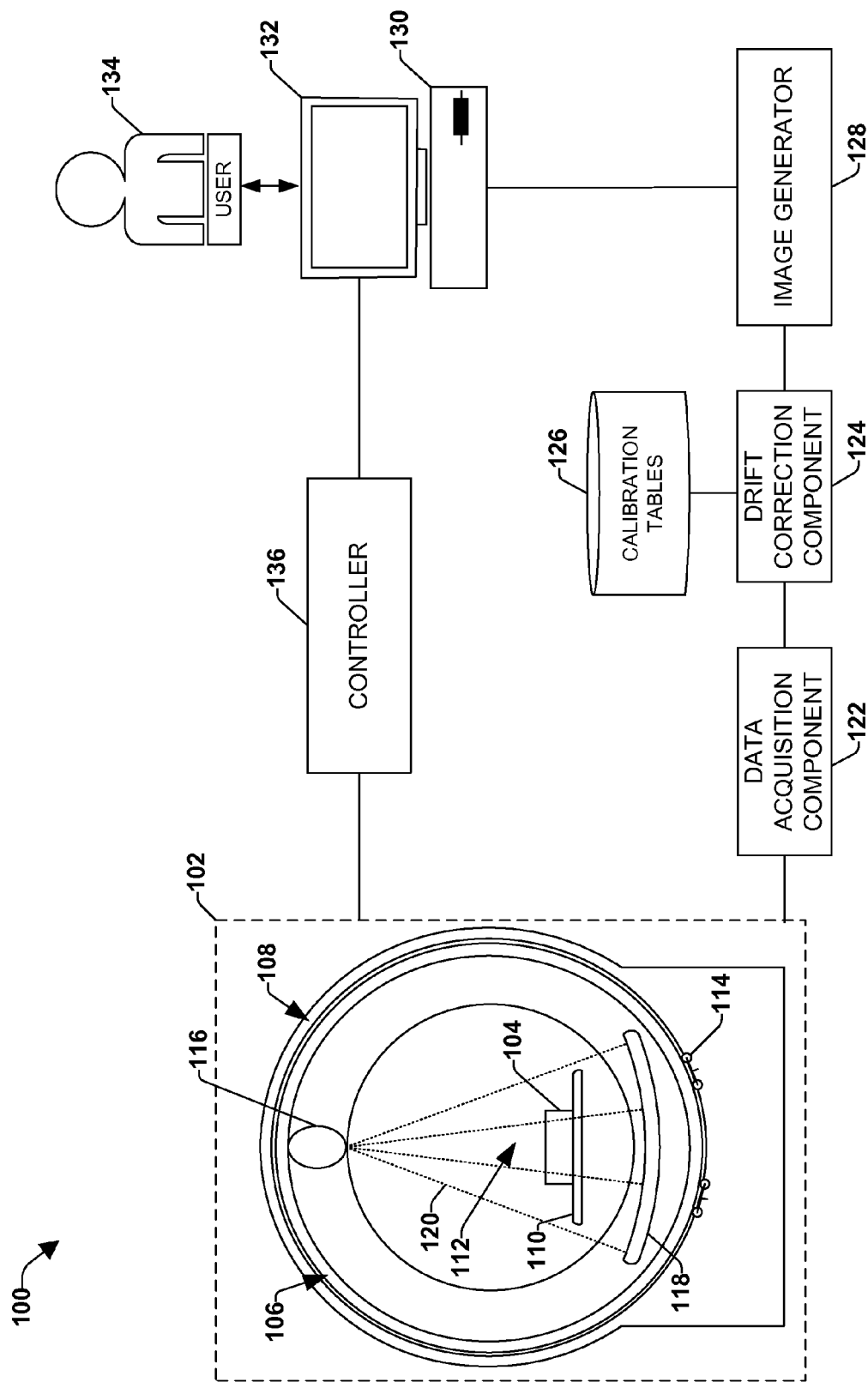
FIG. 1 is a schematic block diagram illustrating an example environment where a radiation system such as described herein may be implemented.

The claimed subject matter is now described with reference to the drawings, wherein like reference numerals are generally used to refer to like elements throughout. In the following description, for purposes of explanation, numerous specific details are set forth in order to provide an understanding of the claimed subject matter. It may be evident, however, that the claimed subject matter may be practiced without these specific details. In other instances, structures and devices are illustrated in block diagram form in order to facilitate describing the claimed subject matter.

One or more systems and/or techniques are provided herein to correct projection data acquired via a radiation system to account for system drift. To measure a degree of drift, a drift calibration is performed according to a desired set of input parameters (e.g., radiation energy level, source current, dosage, etc.) to generate a calibration projection. The calibration projection is compared to a theoretical projection that was expected to be generated based upon the desired set of input parameters and, in some embodiments, based upon the temperature of the radiation system at the time the drift calibration is performed. By comparing the calibration projection (e.g., an actual projection acquired during the drift calibration) with a theoretical projection (e.g., a fictional projection that was expected to be acquired during the drift calibration), a degree of drift can be measured. Such a measurement can subsequently be used to derive a correction factor(s) that can be applied to one or more object projections representative of an object undergoing an examination (e.g., during a non-calibration phase) to correct for system drift.

It may be appreciated that drift calibration, drift calibration phase, and/or the like are used herein to refer to a time window in which the detector array is dark (e.g., a radiation source is emitting little to no radiation) and/or a time window in which at least a portion of a detector array of the radiation system is not masked by an object undergoing examination, and therefore measurements yielded from the unmasked portion of the detector array are indicative of radiation that has traversed air (e.g., and not traversed an object). Thus, in an embodiment, drift calibration may be used herein in a traditional sense to describe a dedicated time in which one or more dark scans and/or air scans are performed for purposes of calibrating a portion of the radiation system, but may also be used in a non-traditional sense to describe any period of time in which less than all of the detector array is masked by an object undergoing examination. For example, in a security application, a drift calibration may refer to a time window between scanning a first bag and a second bag (e.g., where measurements yielded from detector cells that detect radiation that has traversed a gap between the first bag and the second bag are used to generate the calibration projection). As another example, a drift calibration may refer to a time during which a small bag merely masks a center portion of the detector array while an outside edge or parameter of the detector array remains unmasked. Accordingly, in some embodiments, a drift calibration may be performed at the same time that an examination is performed on an object, for example.

The systems and/or techniques provided for herein find particular application to CT systems and/or other radiation systems where the position of at least one of the radiation source or the detector array move or rotate relative to an object undergoing examination. However, the systems and/or techniques may also find applicability to radiation systems where the position of the radiation source and detector array do not move or rotate relative to an object. Further, in some embodiments where the radiation system is a multi-energy radiation system (e.g., configured to emit radiation at multiple, distinct energy spectra), object projection data representative of an object examined via the multi-energy radiation system may be corrected by applying the correction factor(s) to high energy projection data and/or low energy projection data prior to a multi-energy decomposition process.

FIG. 1 illustrates an example environment 100 of a radiation system as provided for herein. It may be appreciated that the example environment 100 merely provides an example arrangement and is not intended to be interpreted in a limiting manner, such as necessarily specifying the location, inclusion, and/or relative position of the components depicted therein. By way of example, the data acquisition component 122 may be part of the detector array 118. Moreover, the instant application is not intended to be limited to use with a particular radiation measurement technique and/or a particular type/class of radiation system. For example, the systems and/or techniques described herein may find applicability to charge-integrating radiation systems, photon counting radiation systems, single-energy radiation systems, multi-energy (dual-energy) radiation systems, indirect conversion radiation systems, and/or direct conversion radiation systems, for example.

In the example environment 100, an examination unit 102 of the radiation system is configured to examine objects (e.g., bags, suitcases, patients, etc.), such as a first object 104. By way of example, the examination unit 102 may be configured to examine a series of bags placed on a conveyor belt and conveyed through the radiation system and/or may be configured to examine patients placed onto a gurney and positioned within an examination region 112 of the examination unit 102.

The examination unit 102 can comprise a rotating gantry 106 and a (stationary) support structure 108 (e.g., which may encase and/or surround at least a portion of the rotating gantry 106 (e.g., as illustrated with an outer, stationary ring, surrounding an outside edge of an inner, rotating ring)). Objects, such as the first object 104, can be placed on a support article 110 of the examination unit 102, such as a gurney or conveyor belt, and conveyed or translated into the examination region 112 (e.g., a hollow bore in the rotating gantry 106) configured to selectively receive objects. The rotating gantry 106 can be rotated about the object(s) during the examination and/or moved relative to the object(s) by a rotator 114, such as a motor, drive shaft, chain, roller truck, etc.

The rotating gantry 106 may surround a portion of the examination region 112 and may comprise a radiation source 116 (e.g., an ionizing radiation source such as an x-ray source or gamma-ray source) and a detector array 118 that is mounted on a substantially diametrically opposite side of the rotating gantry 106 relative to the radiation source 116. In this way, the relative position of the radiation source 116 and the detector array 118 (e.g., the position of the radiation source(s) 116 relative to the detector array 118) may be maintained during an examination of the object(s), for example.

During the examination of an object, such as the first object 104, the radiation source 116 emits fan, cone, wedge, and/or other shaped radiation 120 configurations from a focal spot(s) of the radiation source 116 (e.g., a region within the radiation source 116 from which radiation 120 emanates) into the examination region 112. It may be appreciated that such radiation 120 may be emitted substantially continuously and/or may be emitted intermittently or periodically (e.g., a brief pulse of radiation is emitted followed by a resting period during which the radiation source 116 is not activated). Moreover, the radiation may be emitted at a single energy spectrum or may be emitted at two or more different energy spectra. For example, in one embodiment, the radiation source 116 is configured to alternate between emitting radiation at a first spectrum and emitting radiation at a second spectrum. In another embodiment, the examination unit 102 may comprise multiple radiation sources, where a first radiation source 116 is configured to emit radiation at a first energy spectrum and a second radiation source is configured to emit radiation at a second energy spectrum, for example. In still another embodiment, the radiation source 116 may concurrently emit radiation at a plurality of different energy levels and the detector array 118 may be configured to filter the radiation by energy level, for example.

As the emitted radiation 120 traverses the object 104, the radiation 120 may be attenuated differently by different aspects of the object 104. Because different aspects attenuate different percentages of the radiation 120, an image(s) of the object 104 may be generated based upon the attenuation, or variations in the number of photons that are detected by the detector array 118, or rather detector cells of the detector array. For example, more dense aspects of the object 104, such as a bone or metal plate, may attenuate more of the radiation 120 (e.g., causing fewer photons to strike the detector array 118) than less dense aspects, such as skin or clothing.

Radiation detected by the detector array 118 may be directly converted and/or indirectly converted into analog signals that can be transmitted from the detector array 118 to a data acquisition component 122 operably coupled to the detector array 118. The analog signal(s) may carry information indicative of the radiation detected by the detector array 118 (e.g., such as an amount of charge measured over a sampling period, an energy level of detected radiation, etc.), and the data acquisition component 122 may be configured to convert the analog signals into digital signals and/or to compile signals that were transmitted within a predetermined time interval, or measurement interval, using various techniques (e.g., integration, photon counting, etc.). The compiled signals are typically in projection space (e.g., appearing as sinusoids) and are, at times, referred to as projections. In a multi-energy radiation system, the digital signals may be separated and compiled based upon the energy spectrum of detected radiation represented by the digital signals. Accordingly, in a multi-energy radiation system, high energy projections (e.g., indicative of detected radiation having a high energy spectrum) and low energy projections (e.g., indicative of detected radiation having a low energy spectrum) may be generated from the detected radiation.

For purposes of the instant application, projection, projections, and/or the like may be used in one of multiple (e.g., three) ways. For example, object projections may refer to projections representative of an object undergoing or that underwent an examination. Calibration projections may refer to projections (or portions of an object projection) that are used to measure drift. Calibration projections may be representative of measurements yielded from radiation that traversed air and/or representative of measurements acquired while little to no radiation was being emitted. Theoretical projections may refer to fictitious projections that are expected to be produced from a calibration (e.g., such as a dark calibration or an air calibration) given a set of input parameters and/or given a system temperature of the examination unit 102, for example. It may be appreciated that as previously described, in some embodiments, an object projection and a calibration projection can be acquired concurrently (e.g., simultaneously) where the object masks less than all of the detector array (e.g., such that at least some emitted radiation is detected by the detector array without impinging the object). In other embodiments, it may be desirable to generate a calibration projection at times when an object is not being examined (e.g., such that the object projection and the calibration projection are not acquired concurrently).

The example environment 100 further comprises a drift correction component 124 configured to correct drift in object projections using a correction factor(s) derived from a measured degree of system drift. As may be described in more detail with respect to FIG. 2, the degree of drift is measured by comparing a calibration projection, such as a calibration projection indicative of an air scan (e.g., indicative of radiation that did not pass through an object undergoing examination—although the radiation may pass through a support article 110 or other structural component of the examination unit 102) and/or a calibration projection indicative of a dark scan with a theoretical projection. A difference(s) between the calibration projection and the theoretical projection may be indicative of a degree to which that system has drifted (e.g., away from a reference operating state upon which a set of constraints, such as image constraints, have been based). Based upon this degree of drift, the drift correction component 124 may compute a correction factor(s) that, when applied to an object projection(s), alters measurements associated with the object projection(s) to account for drift (e.g., reducing the effect of the drift on measurements associated with the object projection(s)).

In some embodiments where high energy projections and low energy projections are generated, the drift correction component 124 may be configured to apply a first set of one or more correction factors to the high energy projections and a second set of one or more correction factors to the low energy projections. The set of one or more correction factors applied to the high energy projections may be derived based upon a comparison of a high energy calibration projection to a high energy theoretical projection, for example. The set of one or more correction factors applied to the low energy projections may be derived based upon a comparison of a low energy calibration projection to a low energy theoretical projection, for example. Accordingly, the following techniques may be performed at least twice during a calibration procedure, where the set of correction factors to be applied to high energy projections may be derived during a first iteration and the set of correction factors to apply to low energy projections may be derived during a second iteration, for example.

To compute the theoretical projection(s), the drift correction component 124 is operably coupled to a database 126 configured to store one or more calibration tables, such as air calibration tables and/or offset calibration tables, for example, describing how the radiation system previously behaved during a dedicated set of calibration procedures performed at a manufacturing facility where the radiation system was assembled and/or performed on-site. Such calibration tables may comprise, among other things, offset values and/or gain values that reduce and/or otherwise address the effect of manufacturing defects, electronic noise, etc. on measurements yielded from the detector array, for example.

When a drift calibration is to be performed (e.g., which is different from the dedicated set of calibration procedures from which the calibration tables are derived), the drift correction component 124 is configured to acquire information from the database 126, such as offset values and/or gain values, based upon the desired/specified input parameters to the radiation system during the calibration. Further, as may be described in more detail below with respect to FIG. 2, the drift correction component 124 may be configured to adjust the offset values and/or retrieve offset values as a function of a temperature of the radiation system during the calibration (e.g., where temperature may be an important consideration when determining offset values). Using such gain values and/or offset values, the drift correction component 124 may compute a theoretical projection for the radiation system at the time of the drift calibration. Such a theoretical projection indicates the measurements that were expected to be acquired from an air scan and/or dark scan performed during the drift calibration and may be compared to what was actually acquired during the air scan and/or dark scan to measure a degree of drift and/or compute a correction factor(s) that accounts for the drift.

During an examination of an object(s), the drift correction component 124 may be further configured to apply the correction factor(s) to an object projection(s) to correct one or more measurements associated with an object projection(s) representative of an object(s) undergoing an examination and/or that previously underwent an examination. In this way, measurements acquired from one or more detector cells of the detector array 118 are corrected (e.g., adjusted) to account for system drift. Accordingly, a corrected object projection(s) may be generated by the drift correction component 124, for example.

In the example environment 100, an image generator 128 (e.g., or image reconstructor) is configured to receive the corrected object projection(s) that is output by the drift correction component 124. Such an image generator 128 may be configured to generate one or more images of an object represented by the corrected object projection(s), such as the first object 104, from the corrected object projection data using a suitable analytical, iterative, and/or other image generation technique (e.g., backprojection reconstruction, tomosynthesis reconstruction, iterative reconstruction, etc.). In this way, the data is converted from projection space to image space, a domain that may be more understandable by a user 134 viewing the image(s), for example.

It may be appreciated that where the position of the radiation source 116 and/or the detector array 118 change relative to an object, such as the first object 104, during the examination (e.g., due to the rotation of the radiation source 116 and/or detector array 118 about the object 104), volumetric data indicative of the object 104 may be yielded from the information generated by the detector array 118. Accordingly, the image(s) generated by the image generator 128 may be three-dimensional images (e.g., also referred to as volumetric images), for example. Further, in one embodiment, the image generator 124 may be configured to project the volumetric images to generate two-dimensional images.

It may be appreciated that where the radiation system is configured as a multi-energy radiation system, the environment 100 may further comprise a decomposition component (not shown) operably coupled between the drift correction component 124 and the image generator 128. Such a decomposition component may be configured to utilize one or more high energy corrected object projections representative of an object (e.g., indicative of detected radiation having a first energy spectrum) and one or more low energy corrected object projections representative of the object (e.g., indicative of detected radiation having a second energy spectrum) to compute z-effective values and/or Compton scores for the object and/or aspects thereof using analytical, iterative, and/or other decomposition techniques. In another embodiment, merely one of the high energy object projection(s) or low energy object projection(s) are corrected by the drift correction component 124, and thus the decomposition component receives one corrected object projection and one uncorrected object projection, for example.

The example environment 100 further comprises a terminal 130, or workstation (e.g., a computer), that may be configured to receive images generated by the image generator 128. At least some of the received images may be provided by the terminal 130 for display on a monitor 132 to a user 134 (e.g., security personnel, medical personnel, etc.). In this way, the user 134 can inspect the image(s) to identify areas of interest within object(s) undergoing examination, such as the first object 104, for example. The terminal 130 can also be configured to receive user input which can direct operations of the object examination unit 102 (e.g., a speed to rotate, a speed and direction of a support article 118, etc.), for example.

In the example environment 100, a controller 136 is operably coupled to the terminal 130. The controller 136 may be configured to control operations of the examination unit 102, for example. By way of example, in one embodiment, the controller 136 may be configured to receive information from the terminal 130 and to issue instructions to the examination unit 102 indicative of the received information (e.g., adjust a speed of a conveyor belt).

Figure 2:
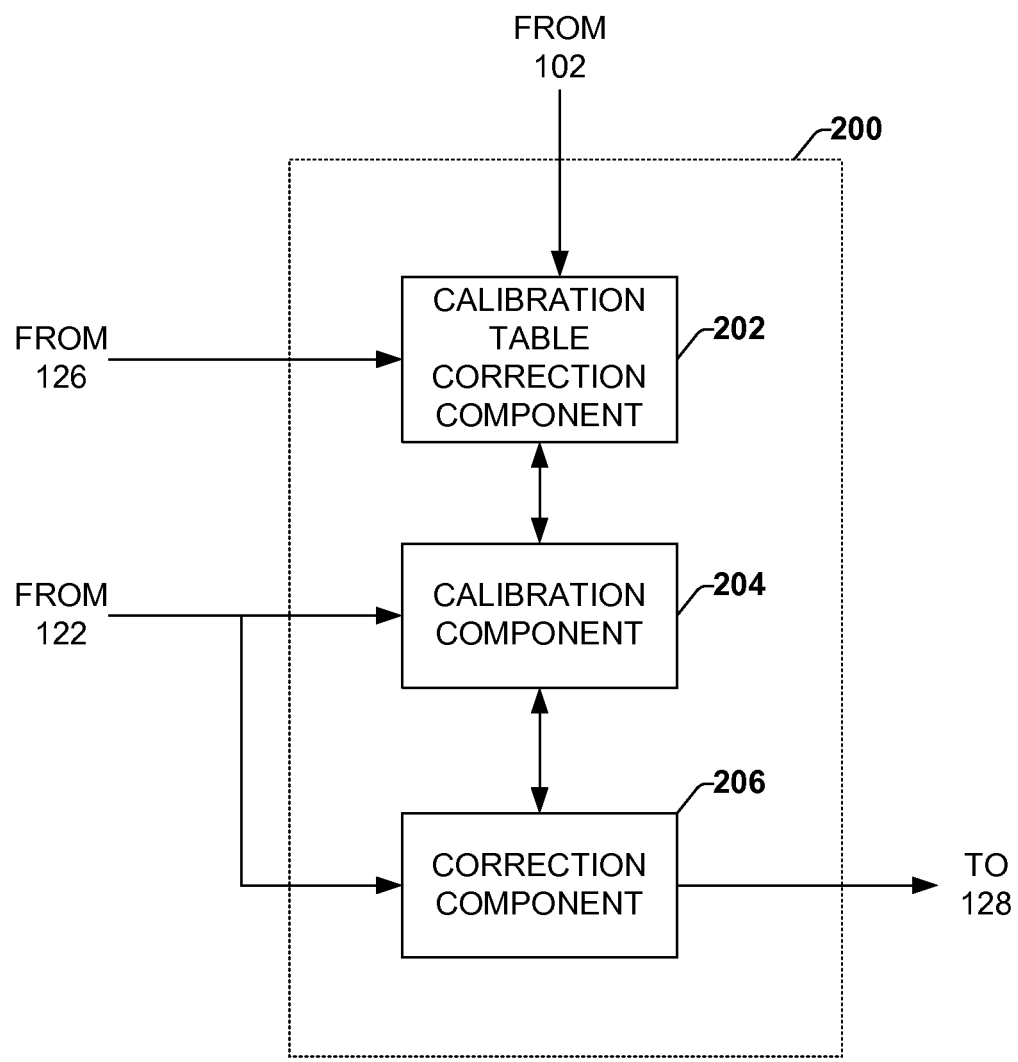
FIG. 2 is a schematic block diagram illustrating an example drift correction component.

FIG. 2 illustrates an example arrangement for components of a drift correction component 200, such as the drift correction component 124 of FIG. 1. It may be appreciated that the components described herein and/or the following arrangements of such components are provided merely as examples. Thus, the instant disclosure, including the scope of the claims, is not intended to be limited to the following embodiments. That is, the drift correction component 200 may comprise other components configured to perform other functions and/or the components described herein may be arranged in a different arrangement from the arrangement provided for herein.

The example drift correction component 200 is primarily configured to perform two roles. The first role is to determine a correction factor(s) to apply to an object projection(s) based upon information obtained from a calibration, and the second role is to apply the correction factor(s) to an object projection(s). The correction factor(s) is configured to correct and/or otherwise adjust measurements associated with the object projection(s) to account for system drift (e.g., to reduce the effect of system drift on the measurements). Accordingly, during a calibration phase, the drift correction component 200 measures a degree of drift to determine one or more correction factors. During an examination phase, the drift correction component 200 applies the one or more correction factors to an object projection(s) acquired from an examination. It may be appreciated that where the calibration phase and the examination phase occur concurrently (e.g., such as when merely a portion of a detector array is masked by an object), the drift correction component 200 may perform both roles concurrently.

To determine one or more correction factors to apply to an object projection(s), the drift correction component 200 comprises a calibration table correction component 202 and a calibration component 204. The calibration table correction component 202 is configured to correct or update one or more calibration tables based upon information regarding an associated radiation system (e.g., input parameters and/or temperature) at the time a drift calibration (e.g., air scan and/or dark scan) is performed to generate a theoretical projection. The theoretical projection is a fictional projection describing how the detector cells are expected to respond (e.g., what measurements the detector cells are expected to output) when radiation is substantially uniformly applied to the detector array and/or when no radiation is emitted, given the input parameters and/or system temperature of the radiation source.

By way of example, the measurements output by respective detector cells of a detector array are expected (e.g., for purposes of image generation) to be the same when an identical amount/energy of radiation is applied to respective detector cells and/or when the detector array is exposed to little to no radiation. However, due to manufacturing defects in the detector cells, electronics, etc., for example, measurements output by some cells may differ from the measurements output by other cells when a same amount/energy of radiation (if any) is applied to respective detector cells. Accordingly, a series of calibration procedures are typically performed to correct for such discrepancies. One such calibration procedure is an air scan from which gain values configured to equalize the measurements are determined and another such calibration procedure is a dark scan from which offset values configured to equalize the measurements are determined. The offset values, gain values, and other values determined/computed based upon the calibration procedures are stored in what are referred to as calibration tables. In some embodiments, the calibration procedures may be performed using various sets of input parameters because such values may differ according to the input parameters. Thus, in some embodiments, a single detector cell may be associated with a plurality of different gain values and/or offset values, where the applicable gain value and/or offset value utilized to correct a measurement during an examination may be a function of the input parameters, for example. It may be appreciated that while the calibration procedures may take into account input parameters (e.g., user specified parameters and/or other controlled parameters), such calibration procedures do not take into account system drift (e.g., uncontrollable or unspecified changes in the system that occur during normal operation).

Accordingly, as provided for herein, the radiation system is configured to intermittently and/or periodically perform a drift calibration, and the drift correction component 200 is configured to determine or update one or more correction factors that are intended to account for system drift (e.g., to reduce the effect of drift on measurements acquired from the detector array). Due to the fluid nature of system drift, a drift calibration may be performed fairly frequently. For example, in one embodiment, a drift calibration is performed every half-hour. In another embodiment, a drift calibration is performed hourly or daily. In still other embodiments, the frequency with which drift calibrations are performed may be a function of the throughput of the radiation system. For example, the radiation system may be configured to perform a drift calibration whenever there is an identified break between objects (e.g., between bags and/or objects being scanned).

When a drift calibration (e.g., such as an air scan or a dark scan) is to be performed, the calibration table correction component 202 is configured to retrieve one or more calibration table(s) from a database (e.g., 126 in FIG. 1) or to retrieve one or more values from the calibration table(s), such as merely offset values, for example. In one embodiment, the calibration table correction component 202 is configured to select a calibration table(s) to be retrieved and/or to select one or more values to be retrieved as a function of input parameters to the examination system at the time of the drift calibration, which may be supplied to the calibration table correction component 202 by the examination unit (e.g., 102 in FIG. 1) and/or a controller (e.g., 136 in FIG. 1). For example, where respective detector cells are associated with a plurality of offset values and/or gain values, the calibration table correction component 202 may be configured to retrieve offset values and/or gain values generated from a calibration procedure(s) performed when the radiation system was operating under a set of input parameters that is similar to the set of input parameters during the drift calibration. It may be appreciated that where the set of input parameters during the drift calibration differs from the set of input parameters during the calibration procedure(s), interpolation and/or extrapolation techniques may be utilized to approximate the offset values, gain values, and/or other values that would have been generated given the set of input parameters during the drift calibration.

The calibration table correction component 202 is further configured to correct or update the retrieved calibration tables and/or retrieved values as a function of the temperature of the radiation system when the drift calibration was performed. For example, one or more temperature sensors may be embedded in the examination unit (e.g., such as at or spatially proximate to a detector spine) and configured to provide a temperature reading(s) to the calibration table correction component 202. The calibration table correction component 202 may be configured to update or correct the retrieved calibration table(s) and/or retrieved value(s) as a function of the temperature of the examination unit when the drift calibration was performed, for example.

By way of example, calibration procedures for a radiation system may be performed when the radiation system is operating at a temperature of approximately 27° C. (e.g., defined as the normal operating point). However, the radiation system may operate at a range of temperatures. For example, in one embodiment, the temperature of a radiation system may vary under normal operation between approximately 23° C. and approximately 35° C., for example. The offset values, gain values, and/or other calibration values that would correct for manufacturing errors, noise, etc. may be different when the radiation system is operating at 23° C. than the offset values, gain values, and/or other values that would correct for manufacturing errors, noise, etc. when the radiation system is operating at 27° C. Accordingly, the calibration table correction component 202 may be configured to use analytic, iterative, or other techniques (e.g., extrapolation, interpolation, etc.) to update or correct the retrieved calibration table(s) or retrieve value(s) based upon the temperature of the radiation system at the time of the calibration.

It may be appreciated that the updated/corrected calibration table or updated/corrected values, such as offset values, gain values, etc., provide information regarding how the detector cells are expected to respond, during the drift calibration, when the detector array is substantially uniformly exposed to radiation (e.g., such as during an air scan) and/or exposed to little to no radiation (e.g., such as during a dark scan). Accordingly, the output of the calibration table correction component 202 may be a theoretical projection (e.g., a projection that is not actually generated by the radiation system) representative of the measurements that are expected to be generated during the drift calibration based upon the corrected calibration table(s) and/or corrected value(s). That is, stated differently, the theoretical projection is representative of measurements that are expected to be generated given the operating temperature and/or the input parameters when the drift calibration (e.g., the air scan and/or dark scan) is performed.

The calibration component 204 of the drift correction component 200 is configured to compare the theoretical projection (e.g., the corrected calibration table(s) and/or corrected value(s)) to an actual projection acquired from a data acquisition component (e.g., 122 in FIG. 1) during the drift calibration to measure a degree of drift. The actual projection acquired during the drift calibration is referred to as a calibration projection and is representative of radiation that did not impinge an object (e.g., such as may occur during an air scan) and/or representative of measurements yielded from the detector cells when the detector cells were not exposed to radiation (e.g., such as may occur during a dark scan). The degree of drift is indicative of a change in operating state of the radiation system (e.g., which is different from a change of input parameters) relative to a reference operating state (e.g., where the reference operating state is the state of the radiation system at the time the set of calibration procedures was performed). Based upon this comparison, one or more correction factors may be determined to apply to an object projection(s) to correct for system drift.

By way of example, in one embodiment, for respective detector cells of the detector array, the calibration component 204 may be configured to compare a theoretical measurement expected to be generated by the detector cell during the drift calibration with an actual measurement generated by the detector cell during the drift calibration. Based upon the difference between the theoretical measurement and the actual measurement, a correction factor for the detector cell may be determined that corrects the actual measurement (e.g., to cause the actual measurement to substantially equal the theoretical measurement after the correction factor is applied to the actual measurement). Such a process may be repeated by the calibration component 204 until a correction factor is determined for respective detector cells.

In another embodiment, the calibration component 204 may divide the detector cells into one or more of regions (e.g., where a region comprises a group of two or more detector cells) and compute a correction factor for respective regions. Various considerations may be applicable when determining a correction factor to be applied to a region of detector cells. For example, in one embodiment, a correction factor for a first region is determined to be a value that causes the lowest standard deviation between the actual measurements (e.g., after the correction factor is applied) and theoretical measurements for detector cells of the first region. In another embodiment, a correction factor for the first region is determined to be a value that causes the fewest number of detector cells to have an actual measurement (e.g., after the correction factor is applied) that differs from the theoretical measurement for the detector cell by more than a specified threshold.

The example drift correction component 200 further comprises a correction component 206. The correction component 206 is configured to receive an object projection(s) from the data acquisition component (e.g., 122 in FIG. 1) and to receive the correction factor(s) from the calibration component 204. Using the correction factor(s), the correction component 206 is configured to correct an object projection(s) representative of an object undergoing an examination or that underwent an examination to generate a corrected object projection. Stated differently, the correction component 206 is configured to apply the correction factor(s) to measurements associated with the object projection(s) to alter the measurements (e.g., correcting the measurements in view of system drift). In embodiments where a single correction factor was determined for the detector array, the correction component 206 may be configured to apply the correction factor uniformly to respective measurements associated with the object projection. In embodiments where a plurality of correction factors were determined, the correction component 206 may be configured to apply a first correction factor to measurements yielded from detector cells associated with the first correction factor and to apply a second correction factor to measurements yielded from detector cells associated with the second correction factor. For example, the correction component 206 may apply a first correction factor to measurements yielded from detector cells comprised in a first region of the detector array and may apply a second correction factor to measurements yielded from detector cells comprised in a second region of the detector array. The corrected object projection may be output from the correction component 206 to an image reconstructor (e.g., 128 in FIG. 1) and/or a decomposition component, for example.

It may be appreciated that where the radiation system is a multi-energy radiation system, high energy object projections and low energy object projections may be generated by the data acquisition component from information provided by the detector array to the data acquisition component. In such embodiments, the correction component 206 may be configured to correct at least one of the high energy object projections or the low energy object projection using the correction factors determined by the calibration component 204. In this way, at least one of the high energy object projections or the low energy object projections are corrected based upon a degree of drift measured by the calibration component 204, for example.

Figure 3:
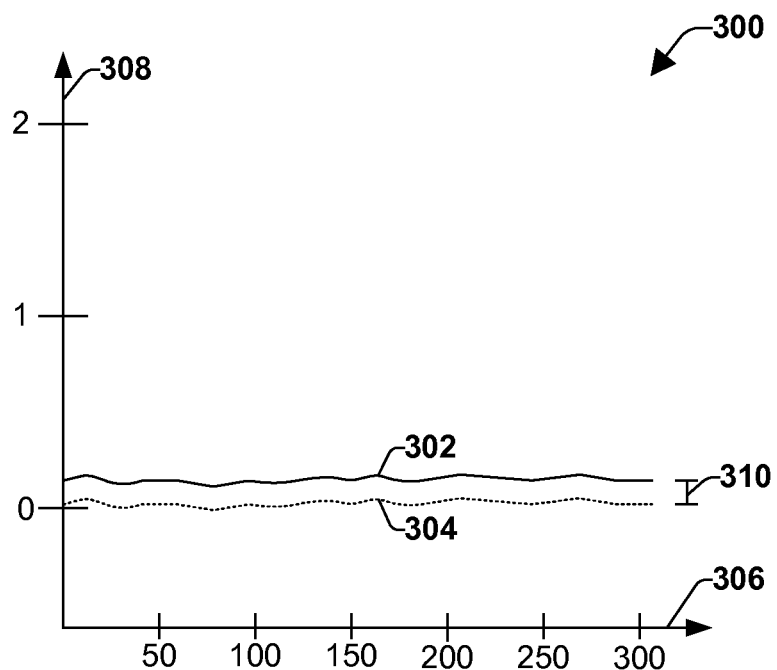
FIG. 3 is a graph illustrating a calibration projection and a theoretical projection.

FIG. 3 provides an example graph 300 illustrating how drift may be computed by comparing a calibration projection 302 acquired when the detector array was substantially uniformly exposed to radiation (e.g., during an air scan) to a theoretical projection 304. The x-axis 306 of the graph 300 represents the detector channel and the y-axis 308 represents magnitude of the projection computed relative to the calibration air scan. Ideally, during an air scan, the projection line should appear as a horizontal line extending from zero. However, in practice, portions of a projection line typically deviate from zero due to, among other things, electronic noise, manufacturing defects in the detector array and/or readout electronics, etc.

The theoretical projection 304 (e.g., as estimated by the calibration table correction component 202 in FIG. 2) represents measurements that are expected to be output by respective detector cells during a drift calibration (e.g., when the input parameters and/or temperature of the radiation system are taken into consideration). The calibration projection 302 represents the actual measurements that are output by the detector cells during the drift calibration. The difference 310 between the theoretical projection 304 and the calibration projection 302 is indicative of a degree to which the system has drifted (e.g., relative to a baseline set of operating conditions at which the radiation system was operating during the calibration procedure). Accordingly, a calibration component (e.g., 204 in FIG. 2) is configured to compute one or more correction factors to correct measurements output by the detector cells (e.g., to substantially match the actual projection 302 to the theoretical projection 304).

Figure 4:
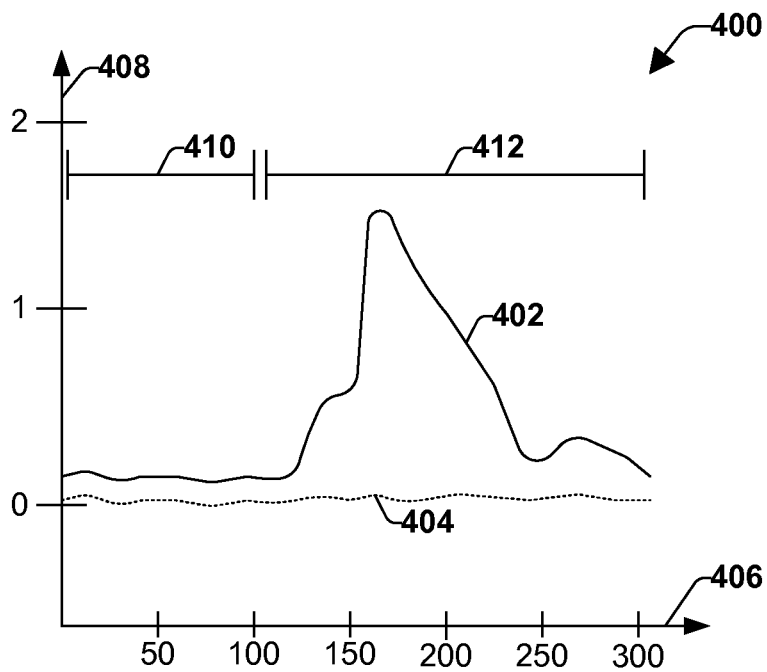
FIG. 4 is a graph illustrating a theoretical projection and a projection comprising a calibration projection portion and an object projection portion.

FIG. 4 provides an example graph 400 illustrating how drift may be computed by comparing a projection 402 to a theoretical projection 404 for an estimated air scan under the same condition. The x-axis 406 of the graph 400 represents the detector channel and the y-axis 408 represents the magnitude of the measured projection. In this example, a first portion 410 of the projection 402 is representative of air (e.g., representative of detector cells that were not masked by an object) and a second portion 412 of the projection 402 is representative of an object. Accordingly, the projection 402 may comprise a calibration projection portion 410 and an object projection portion 412. In such an embodiment, the calibration projection portion 410 may be compared to an equivalent portion of the theoretical projection 404 (e.g., a portion of the theoretical projection 404 respective of the same detector channels as the calibration projection portion 406) to measure a degree of drift and/or determine a correction factor to correct for system drift. In one embodiment, given that some detector cells are masked by the object (e.g., and thus cannot be used by a calibration component to compute a correction factor), a single correction factor may be determined for respective channels of the detector array and/or a correction factor for one or more masked detector cells may be estimated based upon the correction factor for adjacent detector cells, for example.

Figure 5:
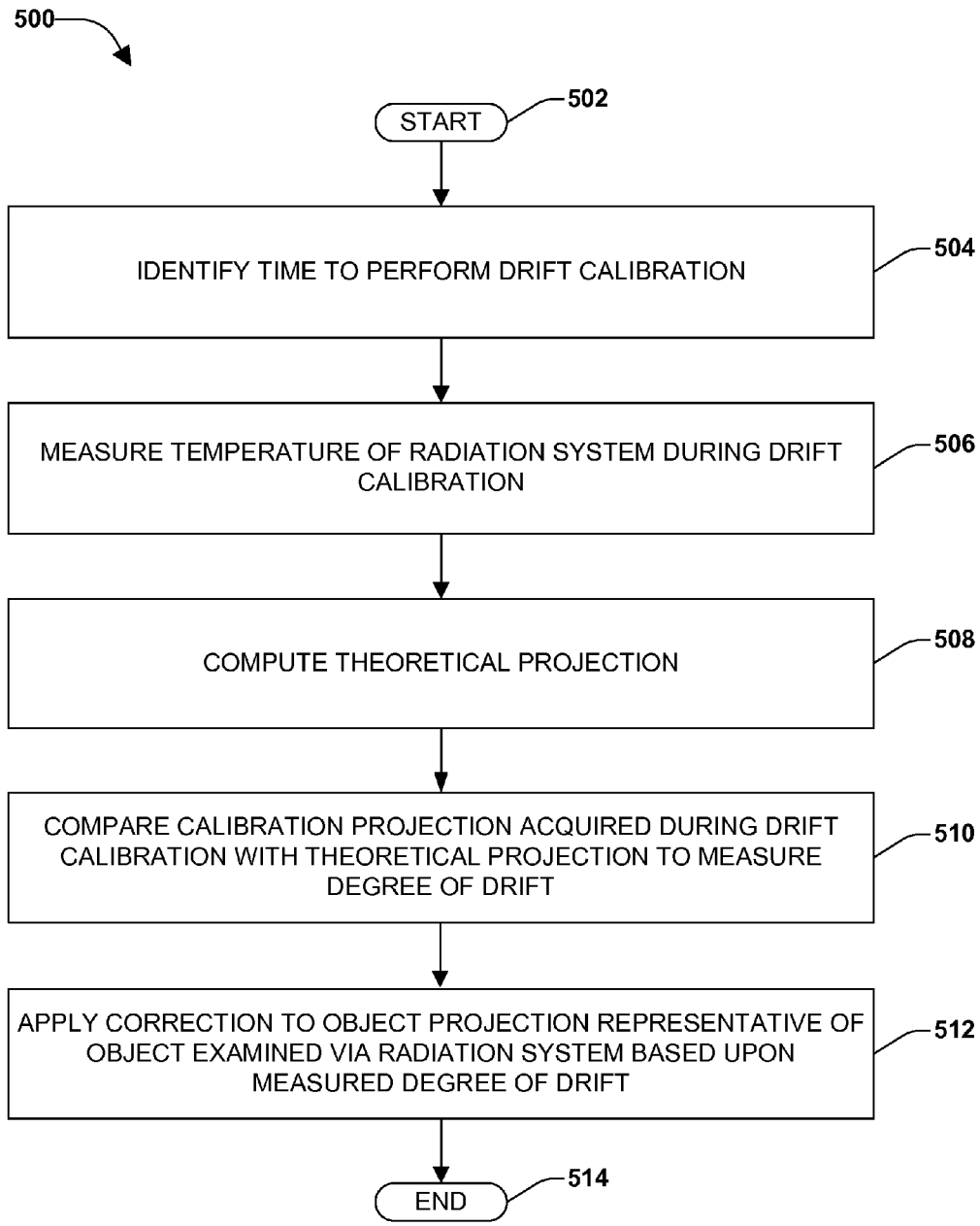
FIG. 5 is a flow chart diagram of an example method for correcting an object projection acquired via a radiation system.

FIG. 5 illustrates a flow diagram of an example method 500 for correcting an object projection acquired via a radiation system, such as a computed tomography (CT) system and/or a multi-energy radiation system (e.g., a multi-energy CT system such as a dual-energy CT system), for example. The example method 500 begins at 502 and a time to perform a drift calibration is identified at 504.

Determining when to perform a drift calibration may be a manual process or may be partially or fully automated. For example, in one embodiment, a schedule is devised for performing drift calibrations (e.g., such as an air calibration to measure drift and/or a dark calibration to measure drift). When the schedule indicates that it is time to perform a drift calibration, operators of the radiation system may be notified to remove objects from the examination area and/or to prevent objects from entering the examination area while an air scan and/or dark scan is performed. In another embodiment, a user may monitor the entrance to a radiation system and initiate a drift calibration when the user identifies a period during which no objects are entering the examination region. In still other embodiments, one or more sensors may be located within and/or spatially proximate to the radiation system to identify periods during which no objects are entering the examination region. When the sensors identify such a period, the radiation system may begin to perform a drift calibration, such as an air scan and/or a dark scan, and/or may request permission from a user to perform a drift calibration. In still other embodiments, the drift correction component may be configured to identify portions of a projection indicative of unmasked detector cells and to initiate a drift calibration using the data from the unmasked detector cells. For example, returning to FIG. 4, a threshold may be set at a measured projection value of 0.25. If a group (of a specified size) of sequentially numbered detector cells respectively measure a projection value of less than 0.25, the group of sequentially numbered detector cells may be determined to not be masked by an object and thus data from the group may be used to measure a degree of drift. Accordingly, in such an embodiment, a drift calibration may be initiated based upon the identification of the group of unmasked cells (e.g., as the portion of the projection associated with the unmasked cells may be utilized to measure the degree of drift). It is to be appreciated that the foregoing techniques for manually and/or automatically determining when to perform a drift calibration are merely example techniques and are not intended to limit the scope of the disclosure, including the scope of the claims.

At 506 in the example method 500, the temperature of the radiation system is measured during the drift calibration. The temperature of the radiation system may be measured using one or more sensors embedded within the radiation system. For example, in one embodiment, the temperature of the radiation system is measured from a sensor(s) embedded within a rotating gantry of the radiation system, such as a sensor comprised at and/or spatially proximate to a detector spine of the detector array. In another embodiment, the temperature of the radiation system may be measured from a sensor(s) embedded within a stationary support structure. In still other embodiments, the temperature may be measured via a sensor(s) external to the radiation system such as an infrared sensor directed toward the radiation system.

In one embodiment, the temperature of the radiation system is monitored substantially continuously and stored in a data structure. Accordingly, when a time to perform a drift calibration is not determined until after the radiation is detected (e.g., such as may occur if the determination to initiate a drift calibration is determined from previously acquired projection data), the temperature of the radiation system during the drift calibration can be retroactively determined. In another embodiment, the temperature of the radiation system is monitored periodically or intermittently and the temperature reading acquired temporally proximate when the drift calibration occurred is acquired from the data structure at 506 (e.g., and thus the temperature measurement may not occur concurrently with the drift calibration, but rather may occur shortly before or after the drift calibration). In still other embodiments, the temperature of the radiation system is merely measured when it is desirable to perform a drift calibration.

At 508 in the example method 500, a theoretical projection is computed. In one embodiment, the theoretical projection is computed based upon the measured temperature of the radiation system at 506. In another embodiment, the theoretical projection is computed based upon input parameters to the radiation system during the drift calibration. In still another embodiment, the theoretical projection is computed based upon the measured temperature of the radiation system at 506 and one or more input parameters to the radiation system during the drift calibration.

To compute the theoretical projection, one or more calibration tables, such as air calibration tables and/or offset calibration tables generated during a set of calibration procedures are corrected/updated based upon the measured temperature and/or the one or more input parameters. By way of example, in one embodiment, offset values and/or for respective detector cells of a detector array of the radiation system are represented in an air calibration table and offset values are represented in an offset calibration table. When the offset values and/or gain values are computed via a set of calibration procedures, the radiation system may have been operated under particular conditions. For example, the radiation system may have been monitored to maintain an operating temperature of 27° C. or other specified operating temperature. Because the values utilized to offset the electronic noise, manufacturing defects, etc. may fluctuate based upon the temperature of the radiation system, the offset values and/or gain values may be adjusted based upon the temperature of the radiation system to determine what the offset values should be when the drift calibration is performed. The corrected offset values, corrected gain values, and/or corrected calibration tables may relate to or describe a theoretical projection that is expected to be generated by the radiation system at the present system temperature. Accordingly, by correcting the offset values and/or gain values and/or by correcting the calibration tables, a theoretical projection for the radiation system (e.g., expected to be generated from an air scan) may be computed given the system temperature during the drift calibration and/or given the input parameters during the drift calibration.

At 510 in the example method 500, a calibration projection, acquired during the drift calibration, is compared with the theoretical projection to measure a degree of drift. That is, stated differently, one or more differences between the calibration projection and the theoretical projection are identified. In one embodiment, an average difference between measurements associated with the calibration projection and theoretical measurements associated with the theoretical projection (e.g., that were expected to be generated by the detector cells of a detector array) is determined based upon the comparison. In another embodiment, for respective detector cells, a difference between what the detector cell actually measured during the drift calibration (e.g., as identified from the calibration projection) and what the detector cells was expected to measure during the drift calibration (e.g., as identified from the theoretical projection or corrected calibration table(s)) is determined based upon the comparison. Accordingly, in such an embodiment, for respective cells of the detector array, a difference is computed. In still other embodiments, the detector cells may be grouped by region and a difference between what a region of detector cells actually measured during the drift calibration and what the region of detector cells was expected to measure during the drift calibration is determined based upon the comparison. Accordingly, by comparing the calibration projection to a theoretical projection, a degree of drift away from a reference operating state (e.g., an operating state of the radiation system at the time of the calibration procedures) can be measured without the aid of a filter or other apparatus that masks a portion of the detector array.

Based upon the measured degree of drift, one or more corrections, or correction factors, can be determined to reduce the effect of system drift on object projections (e.g., to adjust the measurements associated with the calibration projection to substantially match measurements associated with the theoretical projection).

At 512 in the example method 500, the one or more corrections are applied to the object projection representative of an object examined via the radiation system based upon the measured degree of drift to generate a corrected object projection. That is, stated differently, measurements associated with an object projection (e.g., acquired concurrently with the calibration projection or subsequent to the calibration projection) are corrected and/or otherwise adjusted using the one or more corrections to account for system drift (e.g., to reduce the effect of system drift on measurements yielded from an examination of an object). For example, in one embodiment, one or more measurements associated with an object projection are multiplied by a correction factor to increase or decrease the measurements as a function of the measured degree of system drift.

In one embodiment, the corrected projection data is utilized to generate an image representative of the object represented in the projection data. In this way, the corrected projection data is converted from projection space to image space. In another embodiment, the corrected projection data is utilized to perform a multi-energy decomposition process (e.g., to determine a z-effective value(s) for the object).

The example method 500 ends at 514.

It may be appreciated that although not described herein, conventional data correction techniques may be further applied to the object projection(s) prior to applying the correction for drift and/or after applying the correction for drift. By way of example, offset corrections and/or gain corrections may be applied to an object projection prior to applying the correction for drift. Further, convention data correction techniques may be applied to the calibration projection prior to comparing the calibration projection to the theoretical projection, for example.

Figure 6:
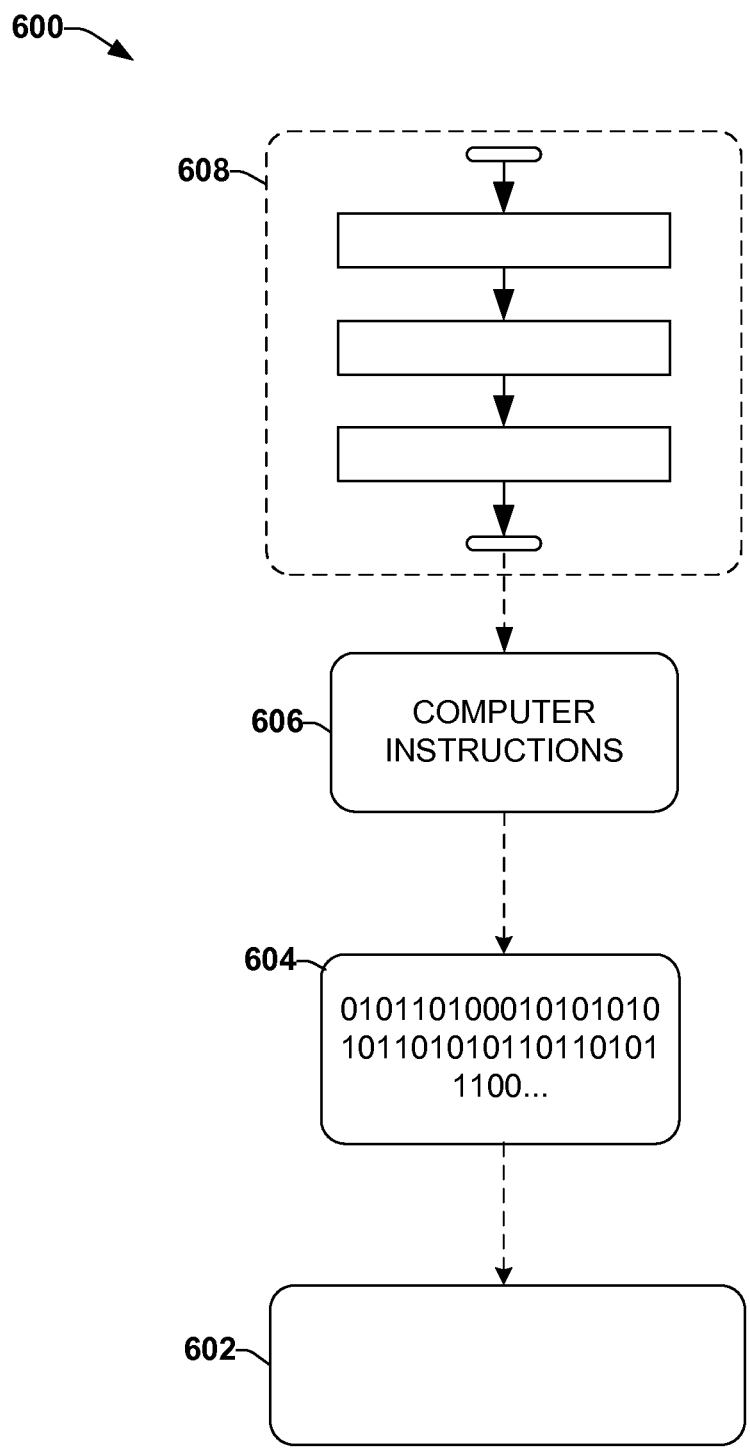
FIG. 6 is an illustration of an example computer-readable medium comprising processor-executable instructions wherein one or more of the provisions set forth herein may be embodied.

Still another embodiment involves a computer-readable medium comprising processor-executable instructions configured to implement one or more of the techniques presented herein. An example computer-readable medium that may be devised in these ways is illustrated in FIG. 6, wherein the implementation 600 comprises a computer-readable medium 602 (e.g., a flash drive, CD-R, DVD-R, application-specific integrated circuit (ASIC), field-programmable gate array (FPGA), a platter of a hard disk drive, etc.), on which is encoded computer-readable data 604. This computer-readable data 604 in turn comprises a set of computer instructions 606 configured to operate according to one or more of the principles set forth herein. In one such embodiment 600, the processor-executable instructions 606 may be configured to perform a method 608, such as at least some of the example method 500 of FIG. 5, for example. In another such embodiment, the processor-executable instructions 506 may be configured to implement a system, such as at least some of the exemplary environment 100 of FIG. 1 and/or the exemplary drift correction component 200 of FIG. 2, for example. Many such computer-readable media may be devised by those of ordinary skill in the art that are configured to operate in accordance with one or more of the techniques presented herein.

Moreover, "exemplary" is used herein to mean serving as an example, instance, illustration, etc., and not necessarily as advantageous. As used in this application, "or" is intended to mean an inclusive "or" rather than an exclusive "or". In addition, "a" and "an" as used in this application are generally be construed to mean "one or more" unless specified otherwise or clear from context to be directed to a singular form. Also, at least one of A and B and/or the like generally means A or B or both A and B. Furthermore, to the extent that "includes", "having", "has", "with", or variants thereof are used in either the detailed description or the claims, such terms are intended to be inclusive in a manner similar to the term "comprising".

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Further, unless specified otherwise, "first," "second," and/or the like are not intended to imply a temporal aspect, a spatial aspect, an ordering, etc. Rather, such terms are merely used as identifiers, names, etc. for features, elements, items, etc. (e.g., "a first channel and a second channel" generally corresponds to "channel A and channel B," where channel A and channel B may be two different channels, two identical channels, and/or the same channel).

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application.

What is claimed is:

1. A method for correcting an object projection acquired via a radiation system, comprising:
   comparing a calibration projection with a theoretical projection to measure a degree of drift; and
   applying a correction to the object projection representative of an object examined via the radiation system based upon the measured degree of drift to derive a corrected object projection.

2. The method of claim 1, comprising performing multi-energy decomposition utilizing the corrected object projection.

3. The method of claim 1, comprising:
   generating an image representative of the object utilizing the corrected object projection.

4. The method of claim 1, the calibration projection indicative of at least one of an air scan or a dark scan.

5. The method of claim 1, comprising:
   measuring a temperature of the radiation system; and
   computing the theoretical projection based upon the measured temperature.

6. The method of claim 5, the computing comprising correcting a calibration table based upon the measured temperature.

7. The method of claim 6, the calibration table comprising at least one of an air table or an offset table.

8. The method of claim 5, the measuring comprising measuring the temperature of the radiation system at a detector spine.

9. The method of claim 1, comprising:
   identifying an unmasked region of a detector array of the radiation system that is not masked by at least one of the object or another object undergoing an examination via the radiation system; and
   generating the calibration projection from information generated by the unmasked region of the detector array.

10. The method of claim 9, comprising:
    upon identifying the unmasked region of the detector array, measuring a temperature of the radiation system; and
    computing the theoretical projection based upon the measured temperature.

11. The method of claim 1, the radiation system comprising a multi-energy radiation system.

12. The method of claim 1, the degree of drift measured without the aid of a filter configured to mask a portion of a detector array of the radiation system.

13. A method for correcting an object projection acquired via a radiation system, comprising:
    measuring a temperature of the radiation system during a drift calibration;
    computing a theoretical projection based upon the measured temperature;
    comparing a calibration projection acquired during the drift calibration with the theoretical projection to measure a degree of drift, the degree of drift indicative of a change in an operating state of the radiation system relative to a reference operating state; and
    applying a correction to a first object projection representative of an object examined via the radiation system based upon the measured degree of drift to derive a corrected object projection.

14. The method of claim 13, comprising applying the correction to a second object projection, the first object projection being a high-energy object projection and the second object projection being a low energy object projection.

15. The method of claim 13, comprising at least one of:
    performing multi-energy decomposition utilizing the corrected object projection; or
    generating an image representative of the object utilizing the corrected object projection.

16. The method of claim 13, the computing comprising:
    correcting a calibration table as a function of the measured temperature of the radiation system during the drift calibration.

17. The method of claim 13, comprising:
    identifying an unmasked region of a detector array of the radiation system that is not masked by at least one of the object or another object undergoing an examination via the radiation system; and
    generating the calibration projection from information generated by the unmasked region of the detector array.

18. The method of claim 13, the radiation system comprising a computed tomography (CT) system.

19. The method of claim 13, the radiation system comprising a multi-energy computed tomography (CT) system.

20. A multi-energy radiation system, comprising:
    a radiation source configured to emit radiation;
    a detector array configured to detect at least some of the emitted radiation to generate at least a high energy object projection representative of an object examined via the radiation system and a low energy object projection representative of the object;
    a calibration component configured to compare a calibration projection acquired from a drift calibration with a theoretical projection to measure a degree of drift, the theoretical projection derived based upon a temperature of the radiation system during the drift calibration; and
a correction component configured to correct at least one of the high energy object projection or the low energy object projection based upon the measured degree of drift.

* * * * *